(12) United States Patent
Makar

(10) Patent No.: US 8,925,135 B1
(45) Date of Patent: Jan. 6, 2015

(54) IMPLEMENT FOR CLEANING AREAS SURROUNDING THE EYES

(71) Applicant: Anthony James Makar, Anchorage, AK (US)

(72) Inventor: Anthony James Makar, Anchorage, AK (US)

(*) Notice: Subject to any disclaimer, the term of this patent is extended or adjusted under 35 U.S.C. 154(b) by 25 days.

(21) Appl. No.: 13/887,328

(22) Filed: May 5, 2013

(51) Int. Cl.
| | |
|---|---|
| A47K 7/00 | (2006.01) |
| A46B 15/00 | (2006.01) |
| A45D 40/00 | (2006.01) |
| A47K 7/04 | (2006.01) |

(52) U.S. Cl.
CPC .................................. *A47K 7/043* (2013.01)
USPC ............... 15/118; 15/106; 15/160; 15/210.1; 132/320

(58) Field of Classification Search
USPC ............... 15/106, 118, 104.001, 159.1, 160, 15/207.2, 209.1, 210.1, 229.14; 132/320; 606/161
See application file for complete search history.

(56) References Cited

U.S. PATENT DOCUMENTS

| | | | | |
|---|---|---|---|---|
| 3,943,592 | A * | 3/1976 | Bhaskar et al. | 15/160 |
| 5,613,262 | A * | 3/1997 | Choy-Maldonado | 15/160 |
| 5,792,159 | A * | 8/1998 | Amin | 606/161 |
| 5,938,673 | A * | 8/1999 | DePierro et al. | 606/161 |
| 6,625,839 | B2 * | 9/2003 | Fischer et al. | 15/160 |
| 6,921,409 | B2 * | 7/2005 | Richard | 606/161 |
| 2009/0131960 | A1 * | 5/2009 | Tanaka | 606/161 |
| 2011/0174328 | A1 * | 7/2011 | Cerutti et al. | 132/200 |

* cited by examiner

*Primary Examiner* — Mark Spisich
(74) *Attorney, Agent, or Firm* — Jeffrey Roddy

(57) ABSTRACT

An implement for the cleaning of areas around the human eye, especially the upper and lower lids and the eye lashes, includes a reusable cleaning implement having at least one low absorbency pad of a soft looped material for cleaning areas adjacent the eye orb wherein the loops of the material capture and remove oils, debris, crusts and cosmetics such as eye liner and mascara. Once laid on a surface, the pad of the article is elevated away from the surface to prevent soiling. The looped material of the pad is cleanable with at least soap and water, and dries rapidly.

4 Claims, 3 Drawing Sheets

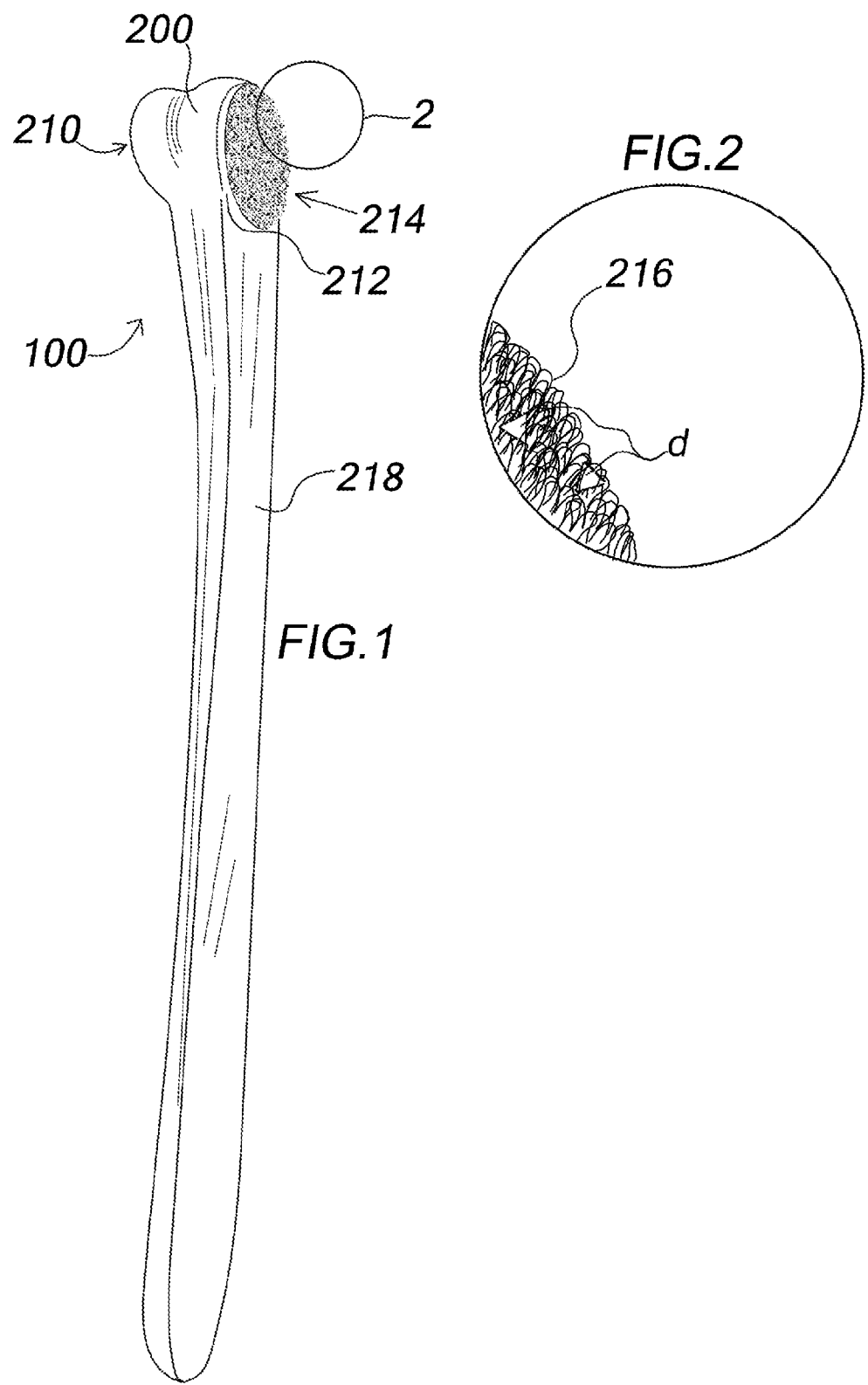

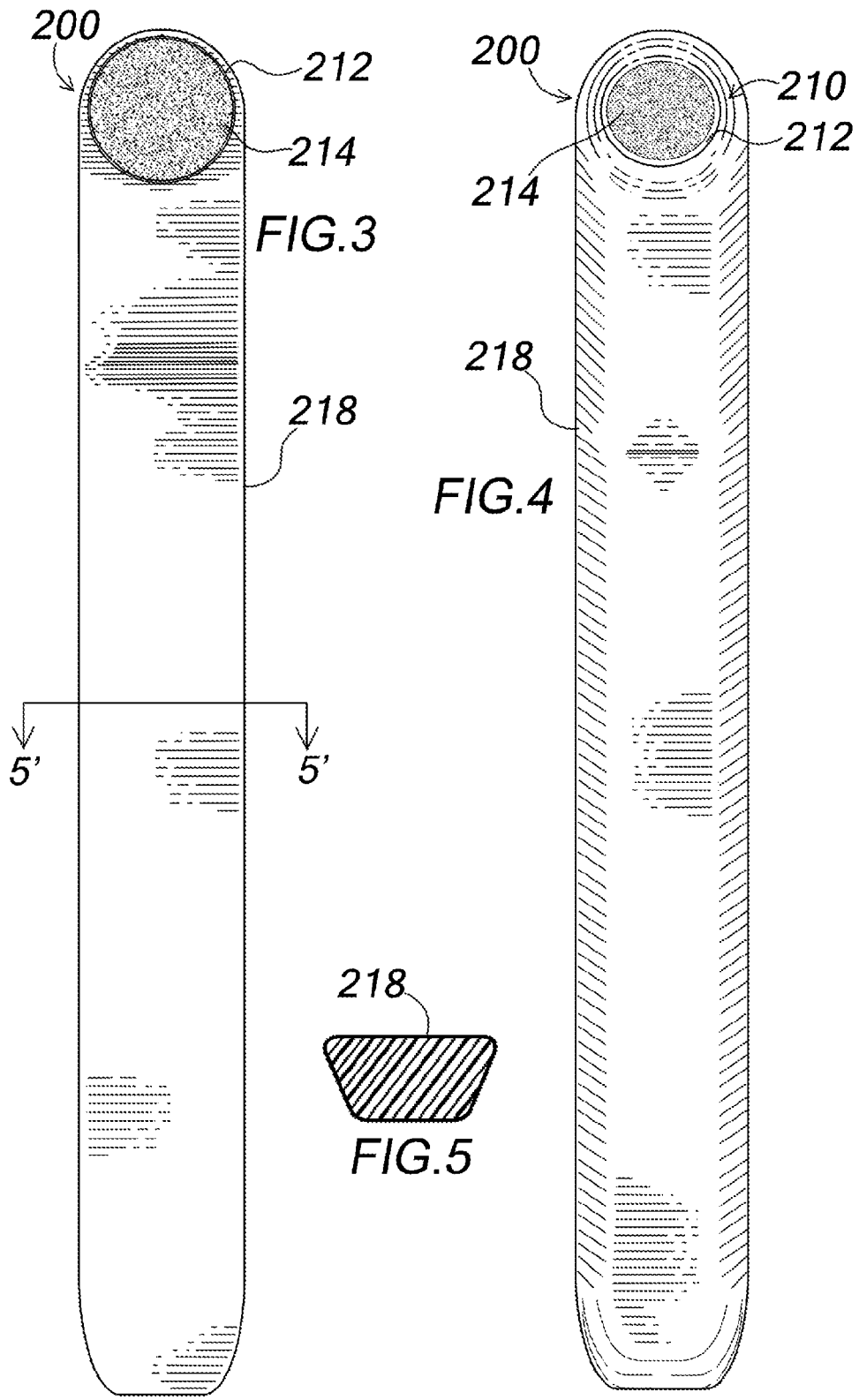

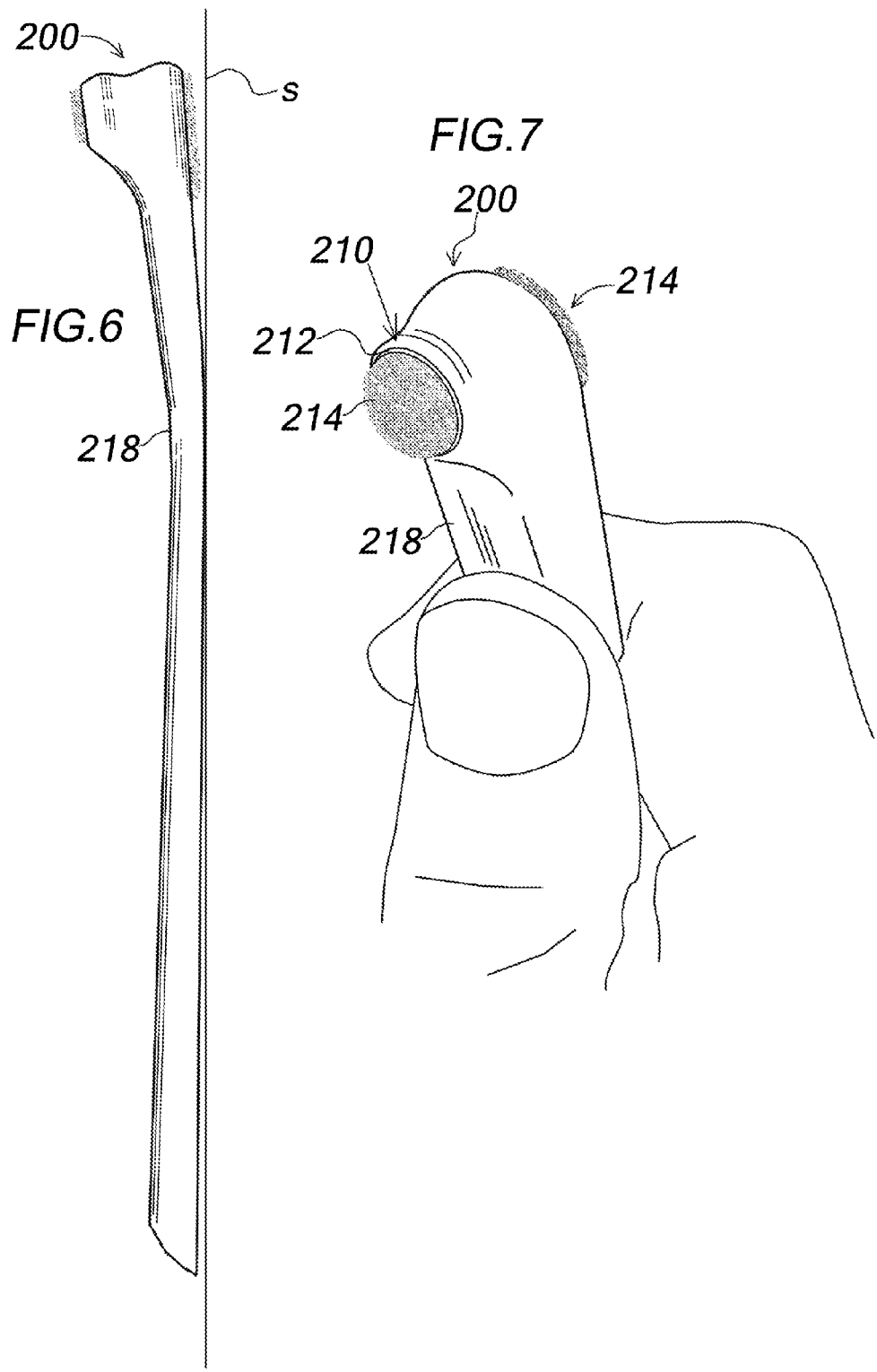

IMPLEMENT FOR CLEANING AREAS SURROUNDING THE EYES

FIELD

The present invention relates generally to cleaning implements, and more specifically to implements for cleaning areas surrounding the human eye.

BACKGROUND

Make-up such as eye liner and mascara can flake and drop into the eye causing irritation and inflammation. Persons suffering from allergies often suffer from dried mucous causing build up on the eyelids. In either case, hygienic practices require the area about the eye to be cleaned thoroughly to avoid complications such as blepharitis, conjunctivitis and inflammation of the tear ducts among other conditions. Several tools for cleaning areas about the eyes; especially swabs and wipes of various design have been described in the past. U.S. Pat. No. 5,509,742 to Balzarini describes a mascara applicator and remover wherein the remover is a beveled detailing tip that is saturated with a mascara remover. U.S. Pat. No. 4,883,454 to Hamburg describes an absorbent swab for use on the eyelids which is infused with an antibiotic. U.S. Pat. No. 4,913,682 to Shabo describes an applicator for scrubbing the eyelid with an absorbent tip which is pre-wetted with a liquid solution. While the foregoing articles work well for their intended use, problems persists. Absorbent materials are difficult to clean and can harbor bacteria and mold which necessitates their one-time use. Although a one-time use article may be indicated in cases of blepharitis, for a healthy person merely desiring to remove old cosmetics or other debris, one-time use is wasteful and costly. Another problem common to past articles is dependency on absorbent materials to remove oils and debris. Removing cosmetics frequently produces both fine and relatively large particles are dislodged, though not retained by absorbent swabs. Accordingly, use of absorbent swabs risks driving larger debris particles into the eye. Also, previous solutions have employed light, and sometimes insubstantial handles such as small tubular plastic, cardboard or wooden sticks that can fold, crumple, break or slip when applying sufficient force to remove, for example, caked on makeup. Accordingly, for at least the foregoing reasons, it would be especially desirable to provide a cleanable and reusable implement which can sufficiently retain oils, dust, and both fine and gross debris of organic or inorganic origin from areas surrounding the eyes. It would be additionally desirable if such an implement possessed an ergonomic handle being sized and shaped to permit sufficient force to be applied while maintaining fine control over the implement.

SUMMARY

The present invention relates generally to an implement for cleaning areas surrounding the human eye including, but not limited to the upper and lower eye lids, lateral angle of the eyes eyelashes, and eyebrows of oils, cosmetics, and both fine and gross debris whether of organic or inorganic origin. The implement is particularly useful for routinely removing eye liner and mascara as well as debris of whatever origin. Stage performers and others routinely using eye make up will find the comfortable looped pad and robust handle easily removes heavy cosmetic build up. The implement includes at least one cleaning pad intended for contact with the skin that includes a low-absorbency or non-absorbent pad of soft looped material that captures and secures debris within the loops. While the soft looped material is preferably a synthetic fabric such as polyester, acrylic or nylon, it can be acetate, modacrylic, olefin or other woven or non-woven synthetic material or a combination of any of the foregoing. Cotton and synthetics having similar absorbency to cotton are to be avoided. While the looped material can be napped or un-napped, when appropriate scrubbing force is applied, the texture is sufficiently rough to dislodge caked on mascara or other adhering debris without causing abrasion to skin. When used as intended the material does not shed fibers and can be cleaned by agitating between the fingers with warm soapy water. The pad material dries quickly minimizing the chance of mold growth.

The implement of the instant invention includes a handle which is joined to a head portion having at least one face topped with a pad of soft looped material which is sized and shaped to permit contact with the folds and crevices about the eye without poking the eyeball. The face is preferably circular or elliptical with a rounded border that extends slightly beyond the edge of the pad. In cases where two pads are used, the pads may have identical texture or differing texture; e.g., napped and un-napped loops, or a thin or thick pile.

In one aspect of the instant invention, an implement includes a head portion that is generally frustum shaped with a planar face at each end, wherein each face is topped by a pad of low-absorbency looped material. The head can be a true frustum or frustoconical wherein the faces are planar, parallel and circular in shape, or a pseudo-frustum wherein the planes of the faces are convergent and at least one face is elliptical. Alternately, the head can be generally cylindrical with a circular or elliptical face at either end wherein each face has the same or different diameter.

In another aspect of the instant invention, an implement includes a head portion that is a truncated cone having a single face topped with a pad of soft low-absorbency looped material.

In yet another aspect of the instant invention, an implement includes a head portion resembling a pair of differing sized frustums joined at their tapering ends, producing a first smaller face at one end, and a second relatively larger face at an opposite end resembling a bobbin with differently sized ends and wherein both faces are topped with a pad of soft low-absorbency looped material.

In all aspects disclosed herein, portions of the head including the borders of the faces are rounded and smooth when transitioning to the other parts of the head, e.g., sides of the head.

In any aspect, the faces of the head are sufficiently distanced from one another so that when the implement is placed on a counter top, the implement naturally assumes a position on its side, thus elevating the face or faces away from the counter top. Portions of the head surround the cleaning pad forming a rim that offsets the material of the pad from potentially soiling horizontal surfaces when laid thereon. A handle connected to the head is angled so that if even if the handle is laid flatly against a counter top, the cleaning pads are elevated away from the counter top.

It will be appreciated by those of ordinary skill in the art and benefit of this disclosure, that the pad material can be integrated with the head by forming or molding into the head, permanently joined to the head, or, can be removable and replaceable. In cases where the pads are replaceable, a new pad can be adhered to the face(s) of the head by a light tack adhesive that can be on the back of the replacement pad or applied separately.

The handle can be of any length, but is sufficiently long so that forceful scrubbing is possible when required. Preferably, the handle has facets or bevels with rounded edges to prevent twisting and turning or slipping when held. This feature is especially advantageous to elderly persons having impaired mobility, or others lacking the fine motor skills necessary to maneuver delicate objects. The handle can be textured with elastomeric dots, ridges or other feature to assist gripping.

The foregoing and other objects, features, and advantages of the invention will become more apparent from the following detailed description, which proceeds with reference to the accompanying figures wherein the scale depicted is approximate.

BRIEF DESCRIPTION OF THE DRAWINGS

FIG. 1 is a side perspective view of a preferred embodiment according to the present invention showing angled head 200;

FIG. 2 is a detail view of the pad showing looped material with entrapped debris (d);

FIG. 3 is a top facing perspective view of one embodiment according to the present invention wherein the upper portion of the handle with pad 214 is parallel with the viewing plane, and the lower portion is angled slightly away from the plane;

FIG. 4 is a plan view opposite that of (FIG. 3) wherein the lower portion of handle 218 is parallel to the viewing plane and upper portion with pad 214 is angled slightly toward the viewing plane;

FIG. 5 is a cross-sectional view taken along lines 5'-5' of (FIG. 3)

FIG. 6 is a side view of a preferred embodiment showing pads of greater and lesser size;

FIG. 7 is an enlarged view showing one end of a preferred embodiment according to the present invention.

DETAILED DESCRIPTION OF THE INVENTION

Reference Listing 100 implement
200 head
210 face
212 border
214 cleaning pad
216 looped material
218 handle

DEFINITIONS

In the following description, the term "reusable" means more than once. The term "cleaning pad" refers to that portion of the cleaning implement described herein which is in contact with the surrounding areas of the eye for cleaning purposes. The term "low-absorbency" relates to the tendency of certain synthetic materials such as acrylic, polyester and nylon to resist saturation either by ionic or non-ionic solutions, and is intended to encompass materials having hydrophobic properties. The term "looped" refers to closed woven material with loops that are napped and randomly spaced or un-napped with regularly spaced loops. Unless otherwise explained, any technical terms used herein have the same meaning as commonly understood by one of ordinary skill in the art to which this disclosure belongs. The singular terms "a", "an", and "the" include plural referents unless the context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety for all purposes. In case of conflict, the present specification, including explanations of terms, will control. In addition, the materials, methods, and examples are illustrative only and not intended to be limiting.

Referring generally to FIGS. 1-7 an implement for cleaning areas surrounding the human eye includes a handle portion 218 and a head 200 portion at one end of the handle. The head portion has a pair of opposing faces 210 which are topped by a cleaning pad 214 of low-absorbency looped material 216 and is rounded, lacking sharp edges or points of contact that could irritate or injure the eye. The pad is preferably circular and when placed atop the face projects anywhere from 2-15 mm from the face which forms a border 212 thereabout. While preferably the head and handle are molded plastic, it can be any sufficiently rigid material appreciated by those skilled in the art and having benefit of this disclosure. The handle is preferably from 4.75 to 7 inches in length and is sized and shaped to permit an individual to apply sufficient force when removing sticky or strongly adhering residues without the handle folding, crumpling or snapping, and without sacrificing the fine control necessary to clean for example, the corners of the eye. Although the preferred embodiment shown herein has two opposing pads, it is conceivable that it possess on a single pad, for example, when replacing a pad.

Turning to FIG. 2, a detail view shows course napped loops 216 that capture and importantly, retain both fine and course debris (d) to keep it from falling in the eyes until such time the implement is thoroughly cleaned.

FIGS. 3 and 4 show a top plan view of one preferred embodiment having a pair of opposing pads 214 in which at least one pad is a low-absorbency looped material. The pads can be similarly sized, or preferably in the embodiment shown, of different diameter. The smaller pad 214 in (FIG. 4) is circular and the underlying face is tilted somewhat out of parallel with the larger face.

FIG. 6 shows a side view of a preferred embodiment with opposing cleaning pads 214 resting in a typical position on a horizontal surface (s) which is shown in the figure as vertical for convenience. Note that the larger cleaning pad is angled slightly away from the surface. The implement is weighted such that when laid in the position shown, the larger pad is elevated away from the potentially soiling surface. If the smaller pad is laid face down on a surface the implement will fall over to the left or right side and elevate both pads away from the potentially soiling surface due to the borders of the head portion shielding the pads. Although the cleaning pads are preferably of a low-absorbency looped material, it is conceivable that one pad of a pair could possess relatively greater absorbency, such as a sponge.

FIG. 6 is an enlarged perspective view showing the relatively smaller sized pad which is preferably from 0.5 to 1.5 cm in diameter, and even more preferably from 1 cm-1.25 cm in diameter. Preferably, the larger pad is 1.0 cm-2 cm in diameter, and even more preferably from 1.25 cm-1.5 cm in diameter. The larger pad is ideal of cleaning the larger curved surface around the eye such as the closed eyelid and eyebrows, whereas the smaller pad enables one to get into the corners about the eye. While the pile thickness of either pad can be anywhere from 1.25 mm to 12 mm, the smaller pad can possess a thicker pile than the larger pad to enable the smaller pad to clean tight corners effectively.

It should be understood that the drawings and detailed description herein are to be regarded in an illustrative rather than a restrictive manner, and are not intended to be limiting to the particular forms and examples disclosed. For example, modifications to the handle texture and number of facets can be altered as required without departing from the scope of the invention. Accordingly, it is intended that the invention encompass any further modifications, changes, rearrangements, substitutions, alternatives, design choices, and embodiments as would be appreciated by those of ordinary skill in the art and having benefit of this disclosure, which fall within the spirit and scope of the following claims.

I claim:

1. A reusable implement for cleaning an area surrounding a human eye, comprising:
   (a) a head portion having first and second opposite planar faces each having a border extending thereabout, the area of the first face being larger than that of the second face, the outline of each of the faces being either circular or elliptical;
   (b) a pair of low-absorbency cleaning pads each adapted for contact with areas surrounding the eye, a first of the pair of pads being larger than a second of the pair of pads, each of the pads including non-shedding soft loops, the large first pad being fastened to the first face of the head portion and the small second pad being secured to the second face of the head portion, and each of the cleaning pads being framed by a respective one of the borders; and
   (c) an elongate handle portion having an end thereof coupled to the head portion, an elongate side of the handle portion on the same side as the first face of the head portion being generally planar and further wherein the handle portion includes a bend intermediate its ends such that when the planar side of the handle is placed on a flat support surface the first pad on the first planar face of the head portion is elevated from the support surface thereby preventing soiling of the first pad.

2. The implement according to claim 1 wherein the loops are woven or non-woven.

3. The implement according to claim 1 wherein the loops are comprised of low absorbency synthetic material.

4. The implement according to claim 1 wherein the loops within a pad are from 2 mm to 10 mm in pile thickness.

* * * * *